United States Patent [19]

Lorenzi

[11] 4,290,016
[45] Sep. 15, 1981

[54] METHOD AND APPARATUS FOR ESTABLISHING MAGNETIZATION LEVELS FOR MAGNETIC PARTICLE TESTING OR THE LIKE

[75] Inventor: Donald E. Lorenzi, Des Plaines, Ill.

[73] Assignee: Magnaflux Corporation, Chicago, Ill.

[21] Appl. No.: 974,009

[22] Filed: Dec. 28, 1978

[51] Int. Cl.³ ............... G01N 27/84; G01R 33/12; G01N 27/72; G01R 35/00
[52] U.S. Cl. ................ 324/216; 324/202; 324/228
[58] Field of Search ............ 324/214, 215, 216, 226, 324/227, 232, 243, 202, 228

[56] References Cited
U.S. PATENT DOCUMENTS 3,495,166  2/1970  Lorenzi et al. ............ 324/238

OTHER PUBLICATIONS

Schroeder "Magnetic Flux Density Measurements Relative to Magnetic Particle Testing", pub. by ASTM Phila. Pa. May 1976 pp. 211-219.
Kraska et al., "Eddy Current Measurement of Magnetic Flux Density", General American Research Division Tech. Report AMFL-TR 72-115, May 1972.
Horstkotte et al., "Magnetic Particle Testing" 10/1945 General Electric Review pp. 24-30.

*Primary Examiner*—Gerard R. Strecker
*Assistant Examiner*—Walter E. Snow
*Attorney, Agent, or Firm*—Neuman, Williams, Anderson & Olson

[57] ABSTRACT

A method and apparatus are provided which are based upon a discovery that regardless of the type of ferromagnetic material of a part and its shape, there is a certain direct, uniform and constant relationship between the level of magnetization required for satisfactory testing by the magnetic particle method and the response which is obtained from an eddy current instrument which has been properly calibrated and which is used under proper conditions. After removal of scale from a surface portion of a part and after demagnetization of the part, a probe of the eddy current instrument is simply placed against such surface portion and the part is magnetized at a level which produces a certain target eddy current indication. The instrument may be readily calibrated through the use of a test block which has a milled slot of a certain size. Preferably, the probe is of a crossed coil type permitting a rapid scanning operation with respect to a plurality of surface areas of a part of irregular shape.

5 Claims, 6 Drawing Figures

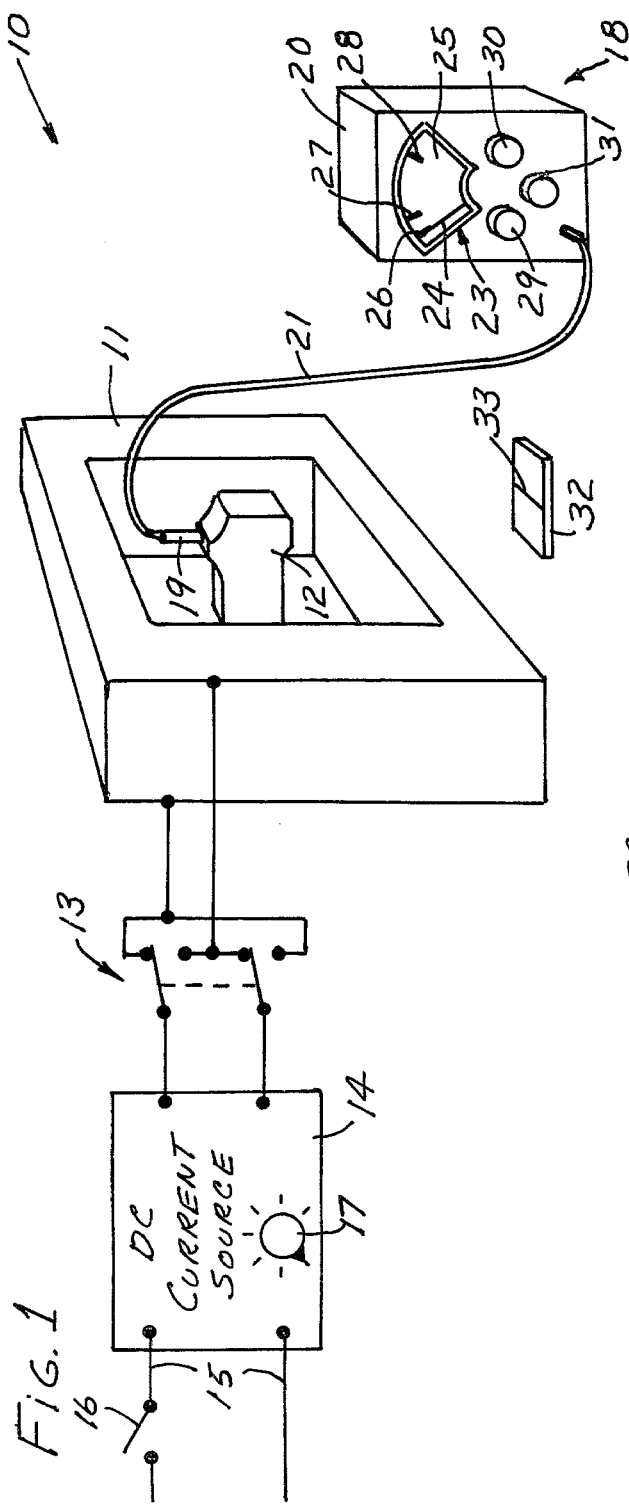
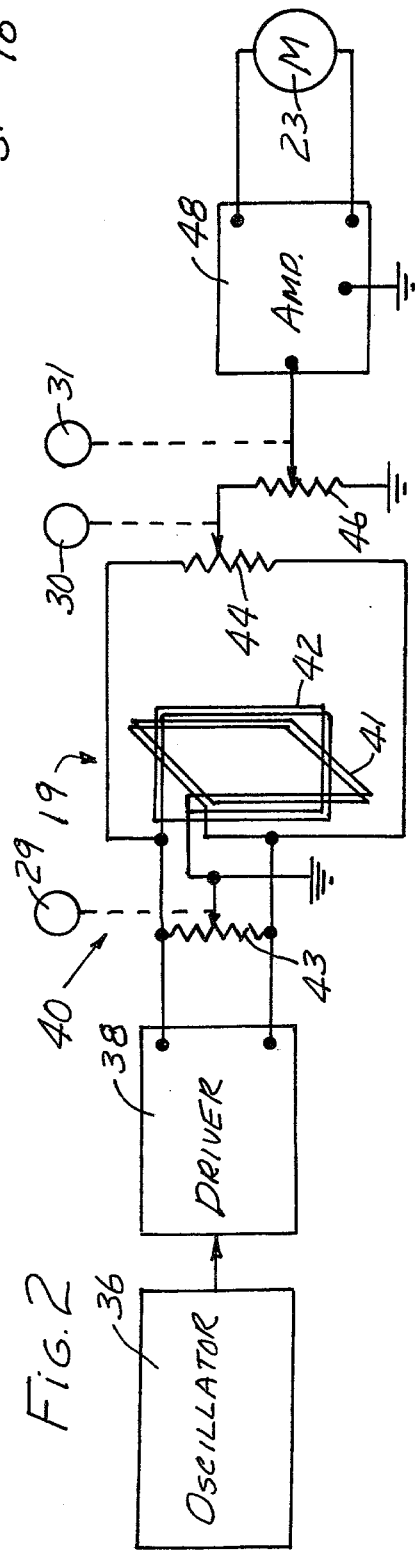

METHOD AND APPARATUS FOR ESTABLISHING MAGNETIZATION LEVELS FOR MAGNETIC PARTICLE TESTING OR THE LIKE

This invention relates to methods and apparatus for use in magnetic particle testing or the like and more particularly to methods and apparatus through which testing of parts of ferromagnetic material can be accomplished in a relatively simple and straight-forward manner, and with minimal chances of error in a manner such as to obtain highly reliable results. The invention is especially advantageous in facilitating the prescription of simple standardized procedures for magnetizing parts at proper levels for detection of defects therein.

BACKGROUND OF THE PRIOR ART

It is well known that defects in parts of ferromagnetic material may be detected by magnetizing the part to cause localized magnetic leakage fields to occur at points on the surface of the part where there are cracks or the like forming magnetic discontinuities. Such leakage fields are detected by dispersing finely divided magnetic particles over the surface of the part, the particles being concentrated at regions where the leakage fields are produced. The leakage fields may also be detected through the use of a suitable leakage field sensing probe, in certain applications.

The results of such testing are used in determining whether a given part will be satisfactory for its intended use and where the part is to be used in a critical application and defects might lead to failure thereof, reliable testing may be essential for safety purposes.

To insure that favorable results from a given test provide an accurate indication that the part is actually free of defects, it is essential that the level of magnetization within a part be of ample magnitude, and various rules and techniques have been used or proposed for this purpose. For example, when a part is to be magnetized by the direct passage of current through the part or through a conductor extending centrally through a part, a rule of thumb is applied that the current should be 1000 amperes per inch of part diameter. This rule is generally satisfactory for small to medium size parts of regular shapes but with large diameter parts, it can result in unnecessarily high amperages and in some cases amperages that are greater than obtainable with existing power pack capabilities.

For coil magnetization, a rule may be applied that the ampere-turn requirements are calculated by dividing 45,000 by the ratio of the length of the part to the diameter of the part. This rule may be applied relatively easily and with good results to simple cylindrically shaped parts but when the parts have complex shapes, determining what actually constitutes the length to diameter ratio can cause confusion.

Instruments have also been used including fluxmeters, Hall effect instruments, artificial crack indicators, and eddy current instruments. The fluxmeter requires a search coil wound around an area where a measurement is to be made and is dependent upon the equal distribution of magnetic flux across the area enclosed by the search coil. Also it requires consideration of the relationship between the measured flux density and the optimum flux density for the particular material being tested.

Hall effect instruments cannot measure the flux density of fields contained within a part and are limited to arrangements in which an opening can be introduced into a part for probe insertion or in which the tangential magnetic field intensity is measured at the surface, the magnetization current being determinable from such a measurement if the magnetic characteristics of the material are known.

Various types of devices have been provided for artificially creating magnetic discontinuities, such devices being placed on the surface of a part that is being subjected to a magnetizing force with the build-up of an indication on the device being used to indicate an adequate magnetizing current. Such devices are of limited reliability, and require a considerable amount of judgment on the part of an operator.

Eddy current instruments have also been proposed for the purpose of measuring magnetic flux density in parts, one disclosure being provided in Technical Report AFML-TR-72-115 of the Air Force Materials Laboratory, Air Force Systems Command, Wright-Patterson Air Force Base, Ohio, May 1972. That report discusses experimental results indicating that a continuous, single-valued, eddy current signal change is generated for changing flux densities in a ferromagnetic steel sample and indicates that heat to heat variations in hardness, stress and cold work do not significantly affect flux measurement by eddy currents. However, it is indicated that gross hardness changes such as encountered in different heat-treated materials will affect the readings and also that the type of steel will affect the readings so that a calibration curve for each type of steel and heat-treat would be required to relate changes in flux density to the eddy current responses. In addition, it would be necessary to control other factors including surface conditions such as scale or work hardening and the magnetic state of the part, as discussed briefly in Schroeder "Magnetic Flux Density Measurements Relative to Magnetic Particle Testing," report on Symposium at the National Bureau of Standards, May, 1976 published by the American Society for Testing Materials.

It is also known that Barkhausen noise impulses are attributed to abrupt changes in the magnetization of a substance when the magnetizing field is gradually altered on the steep part of the magnetization or hysteresis loop, but so far as is known, no application of the effect to magnetic flux density measurements has been proposed.

Still other approaches have been used for attempting to obtain an optimum level of magnetizing current. Operators with a great deal of experience can in many cases make an accurate estimate of the proper amount of magnetizing current when parts to be tested are not highly irregular in shape. It is also possible in some cases to increase the magnetizing current until background indications are obtained and to then "back-off" the current to a certain extent. In addition, it is always possible to try to form a crack in a part of a minimum acceptable size, or to try to find a part having such a defect, and then establish the magnetization level. Such approaches have limitations. Highly experienced operators are not always available and even operators with a great deal of experience can make errors in judgment especially with regard to parts which are highly irregular in shape. Attempting to form a defect for measurement or to find a part having a defect suitable for measurement can be time-consuming and is a procedure which is difficult if not impossible to pursue in many cases.

The result is that practically all parts are tested through the established rules of thumb and there has been no sure and satisfactory way of establishing the proper magnetizing current, especially in the case of parts of irregular shape.

SUMMARY OF THE INVENTION

This invention was evolved with the general object of overcoming disadvantages of prior art techniques and instruments for establishing the optimum level of magnetization within a part and of providing methods and apparatus by which the optimum level of magnetization can be readily established and with a high degree of reliability.

The invention is based in large part upon the discovery of relationships between eddy current responses and the development of leakage field indications such that a standard can be established for readily obtaining optimum magnetizing currents, regardless of the type of ferromagnetic material used in a part and regardless of the shape of the part.

In particular, tests were performed on parts of different materials, using an eddy current instrument after uniformly following certain preliminary procedural steps. It is found that in each case, a certain threshold level of magnetization of substantial magnitude is required to produce any significant eddy current response and that the same threshold level is required to produce any significant magnetic particle indication, even with respect to cracks having a very large depth. With a somewhat higher level of magnetization, the eddy current response is increased and cracks of moderate depth can be indicated through magnetic particles. With a still higher level of magnetization, the eddy current response is increased further and very shallow defects can be indicated through magnetic particles.

The relationship between the threshold and the levels of magnetization at which such responses are obtained vary widely with different types of material and also according to the shape of a part inspected. For example the threshold magnetization level generally occurs when the flux density at a region of the part of interest is of a magnitude corresponding to that at which the material has maximum permeability, and such threshold magnetization levels may thus vary widely with materials having different magnetic characteristics as well as with different shapes of parts.

A very important finding, however, is that the relationship between the eddy current response and the magnetic particle response is substantially constant regardless of the type of ferromagnetic material and regardless of the shape of the part. When in any part the level of magnetization is such as to produce a certain eddy current indication, which may be referred to as a target indication, magnetic particle indications will be obtained as to cracks or seams of very shallow depth, regardless of the type of ferromagnetic material of the part and the shape thereof.

An exact explanation for such findings is not known but based upon such findings, a method and instrumentation are provided for testing of parts in a comparatively simple manner and with a very high degree of reliability.

To obtain reliable results, preliminary steps must be performed. In particular, a part to be tested, or a representative part to be used in establishing the optimum magnetizing current, must be demagnetized prior to testing. Secondly, it is essential that each surface area where an eddy current measurement is to be taken be prepared by removal of any surface scale which is present thereon. Readings obtained on surfaces containing scale were unpredictable and considerably higher than readings obtained from the base metal. It is believed that the electrical and magnetic properties of scale differs very substantially from that of the base metal and that the base metal is the major dependent variable relative to magnetic particle testing. It may also be noted that the suppression of the effects of surface scale is not possible to obtain, even when using eddy current test frequencies as low as 300 Hz.

An eddy current instrument is used including a probe which is placed against the prepared surface areas of the part and including circuitry with which an output response is obtained corresponding to the difference between the response obtained when the part is demagnetized and the response obtained when it is magnetized. The output response so obtained is at the target level when the magnetization is at an optimum minimum value such as to produce indications from shallow seams in a part. As above indicated, the target level will be the same regardless of the type of ferromagnetic material of the part being tested.

The target eddy current response level can be established for any type of eddy current instrument used and, in accordance with a very important feature of the invention, it is established through the use of a test part of prescribed physical characteristics such that highly reliable standards can be established, to be prescribed and adhered to in testing operations.

To further insure reliable results, the probe of the eddy current instrument is preferably such that it has no core, shield or other parts of magnetic material which would make the probe sensitive to magnetic fields in air.

Conventional absolute probes may be used in which an eddy current response is balanced against a fixed reference such as a reference voltage or current which is established by obtaining a null indication with the probe disposed against a prepared surface portion of a demagnetized part. Preferably, however, and in accordance with a specific feature of the invention, a probe is used having coils which are crossed, one coil being positioned for measuring with respect to fields transverse to the magnetizing field and being operative to produce a reference, the other coil being used for measuring with respect to fields in the direction of magnetization. The advantage of this type of probe is that a reasonably stable balance can be obtained to permit a scanning operation. Thus the probe may be moved from one prepared surface portion of a part to another to check the responses obtained thereat, without any rebalancing operation. With an absolute probe, on the other hand, the part should be demagnetized and the instrument should be rebalanced for each new probe placement.

Important features of the invention relate to the provision of an instrument for use with a standard test member and having indicating and adjustment means such as to permit periodic calibration to insure that the target eddy current response level will be reliably obtained. A sensitivity adjustment means is provided for adjusting sensitivity to obtain a certain calibration indication when the probe is placed against a test member which, for example, may be in the form of a block of ferromagnetic material having a milled slot therein of a certain target indication corresponding to the target eddy current response level. The standard test member may be such that the target and calibrations are the same or may preferably be such that the calibration indication is substantially higher than the target indication. For example, the calibration indication may be on the order of four times the target level indication.

This invention contemplates other objects, features and advantages which will become more fully apparent from the following detailed description taken in conjunction with the accompanying drawings.

BRIEF DESCRIPTION OF THE DRAWINGS

FIG. 1 diagrammatically illustrates a magnetic particle inspection system and an eddy current instrument for establishing the level magnetization according to the invention;

FIG. 2 is a schematic diagram of the eddy current instrument of FIG. 1;

DESCRIPTION OF A PREFERRED EMBODIMENT

Figures 3, 4, 5, 6:
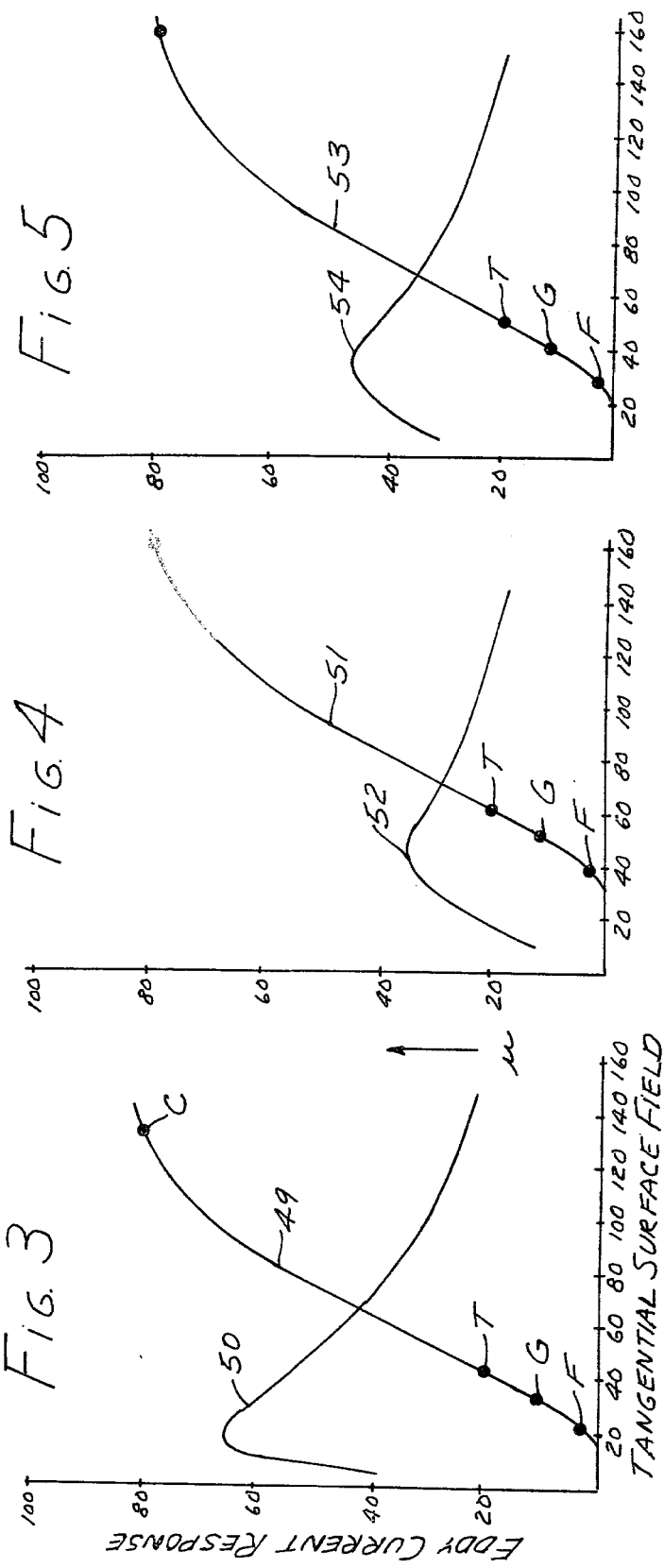
FIG. 3 is a representative graph for one type of material, illustrating the relationship of eddy current response, magnetic particle indications and permeability as a function of tangential magnetic field intensity.
FIG. 4 is another representative graph like FIG. 3 but for another type of material.
FIG. 5 is another representative graph like FIGS. 3 and 4, for still another type of material.
FIG. 6 diagrammatically illustrates an inspection system using a leakage field sensor, constituting another type of inspection system with which the method and instrumentation of the invention is usable.

FIG. 1 diagrammatically illustrates a magnetic particle inspection arrangement which is generally designated by reference numeral 10 and which includes magnetizing means in the form of a coil 11 arranged to surround a part 12 to be inspected for defects. The coil 11 is connected through a reversing switch 13 to a DC current supply 14 which is connected through conductors 15 and a switch 16 to an AC supply. As diagrammatically illustrated, the DC current supply 14 is adjustable by means of a knob 17, to adjust the current supplied to the coil 11. When the current supplied to the coil 11 is of sufficient magnitude, magnetic particles can be dispersed over the surface of the part 12 to be concentrated in any areas in which there are cracks or similar defects which produce localized leakage fields. It is noted that magnetization means other than a coil such as the coil 11 may be used and, for example, current may be passed through a part or a part may be disposed between poles of a yoke structure having an energizing coil thereon.

It is very important that the magnetization level be sufficient to produce strong leakage fields and corresponding indications with respect to any cracks or other flaws of a size greater than a minimum size which can be tolerated in the part under test. At the same time, it is undesirable to use an excessively high level of magnetization which can obscure indications and also result in a waste of energy and equipment as well as imposing unnecessarily high demand requirements on the electrical supply system.

In accordance with this invention, an eddy current instrument 18 is provided for measuring the level of magnetization of a part. The instrument 18 includes a probe 19 which is placed against a surface portion of a part such as the illustrated part 12 and further includes energization and indicating means in a unit 20 to which the probe is connected through a cable 21.

The unit 20 includes a meter 23 having an indicator 24 and a scale 25 which has marks thereon including a zero or null mark 26, a target level mark 27 and a calibration mark 28. The unit 20 has manually operable controls including balance knobs 29 and 30 and a sensitivity adjustment or calibration knob 31. Also associated with the instrument 18 is a test block 32 which has a milled slot 33 therein and which forms a calibration standard.

Testing is readily accomplished in a simple and straightforward manner. An initial step is to prepare the part to be tested or a representative part in a typical case in which a number of parts of the same type are to be tested. A demagnetized condition of the part must be established and if the part is not in a demagnetized condition, it may be demagnetized by separate demagnetizing apparatus or by use of the reversing switch 13 and current control knob 17 in the equipment as diagrammatically illustrated, sequentially applying magnetic fields of alternating polarity and of amplitudes which gradually decrease from a saturation magnitude to a very low magnitude.

In addition to establishing a demagnetized condition, it is also important in preparing a part to establish base metal characteristics at at least one surface portion of the part. Typical ferromagnetic parts to be tested have scale formed on the surface thereof which must be removed if reliable results are to be obtained. It is found that eddy current readings obtained over surfaces containing scale are unpredictable and usually considerably higher than readings obtained from base metal, whereas leakage fields from cracks or the like are primarily dependent upon the base metal characteristics. It is also found that it is not possible to adequately suppress the effects of surface scale, even when using eddy current test frequencies as low as 300 Hz. Accordingly, it is very important that any existing surface scale be removed to establish base metal characteristics.

It is not necessary to prepare the entire surface of the part but only such surface portions at which the magnetization level might possibly be of reduced magnitude, surface portions at which stress concentrations are possible and surface portions where the existence of a crack or other defect is critical. In parts of irregular shape, portions which project transversely relative to the primary orientation of the magnetic field in the part may have a magnetization level of reduced magnitude and hence preparation of a surface portion thereat is in order.

In addition to preparation of one or more surface portions of a part, calibration and balancing of the instrument 18 should be performed before tests are made for the purpose of establishing the proper magnetization level, it being noted that one calibration procedure and/or one balancing procedure may be sufficient in many cases for a number of subsequent testing operations.

To calibrate and balance the instrument 18, the probe 19 is disposed on a portion of the test block 32 spaced from the milled slot 33 and the balance knobs 29 and 30 are adjusted to obtain a null reading at which the indicator 24 is positioned in alignment with the null mark 26 on the scale 25. Then the probe 19 is positioned over the milled slot 33 while the sensitivity adjustment or calibration knob 31 is adjusted to position the indicator 24 opposite the calibration mark 28. During this calibration operation, the position and orientation of the probe may be adjusted to obtain a maximum indication, the probe preferably being a crossed coil type of probe as hereinafter described.

To establish the proper magnetization level for testing of the part 12, the probe 19 is placed on a prepared surface area of the part and, before applying a magnetizing current, the balance of the instrument may be checked and readjusted if necessary by adjusting knobs 29 and 30 to position the indicator 24 in alignment with the null mark 26 on the scale 25. Then magnetizing current is applied by closing switch 16 and adjusting knob 17 to gradually apply an increase in current while noting the deflection of the indicator 24 and while adjusting the orientation of the probe to maximize the deflection of the indicator 24. It will be found that the indicator 24 will not move substantially until the level of magnetization is increased above a certain level and after the indicator 24 starts to move, the current is increased until the indicator 24 is positioned in alignment with the target level mark 27.

In cases in which a plurality of surface areas have been prepared, the probe may be placed on each such area with the magnetization current being increased, if necessary, to effect alignment of the indicator 24 with the target level mark 27. It is noted that the level of magnetization should be such as to cause the indicator 24 to at least reach the target level mark 27 as to all surfaces of interest and if the indicator 24 moves beyond the mark 27 as to some of such areas, it will not adversely affect subsequent testing operations.

After the proper level of magnetization is established, the part 12 and all parts having the same shape and of the same material may be inspected by placing them in the coil 11, in the same position and orientation as when testing for the proper level of magnetization, and the parts may then be inspected by dispersing magnetic particles over the surface thereof to be attracted and concentrated by leakage fields at surface areas where there are underlying cracks or similar inhomogeneities.

Referring to the schematic diagram of FIG. 2, the instrument 18 includes an oscillator 36 which is coupled through a driver stage 38 to a bridge circuit 40. The probe 19 is part of the bridge circuit 40 and is preferably of a crossed coil type which has been used extensively in a different application, for detection of cracks. The probe 19 includes a pair of coils 41 and 42 having operative axes which are at right angles to each other and in a plane parallel to the surface of the part. By way of example, the probe may be constructed as disclosed in the Lorenzi et al U.S. Pat. No. 3,495,166 and may include a bobbin including crossing narrow slits in one end face which receive crossing portions of the coils for placement in close proximity to a surface of the part.

In addition to the coils 41 and 42, the bridge circuit 40 includes potentiometers 43 and 44 which are connected to output terminals of the driver stage 38 and which form balance adjustment elements, the movable contacts thereof being mechanically coupled to the knobs 29 and 30. The coils 41 and 42 are connected in series between the output terminals of the driver stage 38 and the movable contact of the potentiometer 43 is connected to the junction therebetween while the movable contact of the potentiometer 44 is connected to a potentiometer 46 which forms a sensitivity control element. The movable contact of potentiometer 46 is connected mechanically to the knob 31 and is connected electrically to the input of an amplifier 48 the output of which is connected to the meter 23.

In operation, an alternating current flows through both of the coils 41 and 42 at a frequency which may, for example, be on the order of 100 KHz but which is not critical. When the probe is placed against a part, the alternating current through the coils induces fields in the part to cause eddy currents to flow therein and such eddy currents, in turn, produce fields which induce electromotive forces in the coils 41 and 42. The overall result is that the effective impedances of the coils are functions of the permeability, conductivity and other characteristics of the material of the part as well as the spatial relationship and orientation of the coils relative to the part. It is found that the eddy current effect and hence the impedance of each coil are affected by unidirectional magnetic fields within the part. With the axis of one of the coils in alignment with an applied magnetic field and with the axis of the other coil transverse to the applied field, an unbalance is produced if the magnetic field is of sufficient magnitude. At the same time, characteristics of the part which are not effected by the applied magnetic field and which have no orientation characteristics will produce equal responses in the two coils and will not contribute to any difference between the impedances of the coils.

In operation, the probe 19 may be placed against a prepared surface portion of a part and the bridge 40 is balanced by adjustment of the knobs 29 and 30 to adjust the potentiometers 43 and 44, no output being produced by the meter 23. When through the application of a magnetic field to the part, an unbalance is produced, it is amplified by the amplifier 48 and applied to the meter 23. The probe 19 is rotated to produce a maximum output, the axis of one coil thereof being then effectively aligned with the applied field while the axis of the other coil is effectively transverse to the applied field.

It is noted that the use of the crossed coil type of probe is advantageous in that the instrument is highly stable with respect to balance, the response of the two coils being equally effected by changes in the spacing of the probe relative to the surface of part and changes in permeability and other characteristics of the part. Also, it is possible to use the probe in a scanning operation in which after establishing a demagnetized condition of a part, the probe can be moved from one surface portion of a part to another to check the effect of the magnetization levels thereat, without reestablishing the demagnetized condition. Absolute types of probes, in which the signal produced across the coil is compared with an adjustably fixed reference, would require demagnetization prior to checking of the effect of the magnetization level at each prepared surface portion.

It is also noted that in any case, whether using a crossed coil type of probe or an absolute type of probe, it is important that the probe be free of any core or shield structure of a magnetic material because such will cause the probe to be sensitive to external fields and will adversely effect the reliability of the testing operation.

Referring to FIG. 3, the relationship between the eddy current response and the level of magnetization for a certain type of material is indicated by a line 49, the eddy current response being indicated in arbitrary units of from 0 to 100 while the magnetization level is indicated by the tangential surface field, measured in oersteds. The relationship of permeability to the tangential field intensity for the same material, is indicated by line 50. It is noted that there is no eddy current response until the field intensity is nearly equal to 20 oersteds, but when the tangential field is increased above 20 oersteds, the eddy current response increases in proportion to the increase in the tangential field until a relatively high intensity field is applied, when the eddy current response starts to flatten out. It is also noted that the eddy current response starts to occur at a field intensity which is somewhat above that at which the permeability of the material is at a maximum and, apparently, the ultimate flattening out of the eddy current response is due to magnetic saturation of the material.

With regard to the relationship between the eddy current response and the magnetic particle inspection response, a faint magnetic particle indication is obtained with the material tested at a tangential field intensity of about 20 oersteds, at the point indicated by reference character F on the eddy current response curve 49. At a tangential field intensity of about 30 oersteds, a good magnetic particle indication is obtained, as indicated by reference character G on the eddy current response curve 49. At a tangential field intensity of about 40 oersteds, a very good magnetic particle indication is obtained, at a point indicated by reference character T on the eddy current response curve 49 such being an optimum or target point.

In FIG. 4, reference numerals 51 and 52 respectively designate eddy current response and permeability curves for another type of material and reference characters F, G and T indicate the points at which faint, good and very good or target magnetic particle indications are obtained for such material. Similarly, in FIG. 5, reference numerals 53 and 54 indicate the eddy current response and permeability curves which might be obtained with a third type of material and reference characters F, G and T again indicate the points at which fair, good and very good magnetic particle indications are obtained for such material.

It is noted that in the type of material to which FIG. 4 relates, no eddy current response is obtained until the tangential field intensity is above 30 oersteds. The permeability of the material is less than that for the curves of FIG. 3 and the point at which the eddy current response starts to occur is again at or slightly above the maximum permeability point. The characteristics depicted in FIG. 5 are about mid-way between those depicted in FIGS. 3 and 4.

The relationship which is of primary importance to the method and apparatus of this invention is the relationship between eddy current response and magnetic particle indications obtained. It is noted that in each case, a faint magnetic particle indication is not obtained until the magnetic field is increased to a point where the eddy current response starts to occur. A good magnetic particle indication is obtained in each case at about the same level of eddy current response, i.e. at a level of about 10 in the arbitrary response units used in the measurements in question. The very good magnetic particle indications are likewise obtained at the same eddy current response levels, in each case a reading of about 20 units. Such relationships are obtained regardless of the type of ferromagnetic material tested and, as a result, it is not necessary to calibrate the instrument for each type of material tested and, once calibrated, the instrument is usable for determining the proper magnetization level for any type of ferromagnetic material.

Any one of a number of types of calibration standards could be used but one which has been found to be very convenient and otherwise advantageous is the test block 32 which may be a flat member of tool steel having a thickness of 0.125 inches, a width of 1.5 inches and a length of 3 inches with the milled slot 33 being 0.01 inches wide and 0.1 inches deep. The material may be flat tool steel, precision ground, with oil hardening. The milled slot 33 produces an eddy current response which is about four times the optimum or target response required to produce very good magnetic particle indications in all types of ferromagnetic material. Thus, with reference to the graphs of FIGS. 3–5, the milled slot 33 may produce a reading of 80 in the arbitrary response units used in conjunction with FIGS. 3–5. Reference character C indicates the calibration point in FIGS. 3–5. It is noted that the calibration standard could be so constructed as to produce a response equal to the target response but the use of a standard which produces a calibration response substantially greater than the target response has an advantage. In particular, the magnetization level can be increased substantially above the level at which the target response is obtained, but if the magnetization level is too high, magnetic particle indications may be obscured and other deleterious effects may be obtained. The calibration point can serve to indicate, at least roughly, the upper limit of magnetization. Thus, the magnetization level may be increased to a point at least equal to that at which the target indication is obtained and so long as it is kept below the point at which the calibration indication is obtained, the results should be satisfactory.

It should be noted that the target level of magnetization is adequate for detection of very shallow cracks having a depth of less than 0.01 inches but where the allowable size of defects is greater, a lesser level of magnetization may be used. Thus a level of from 25% to 50% of the target level may be adequate for seams having a depth of 0.015 inches or greater, using the magnetic particle detection method. A level below 10% of the target level is generally inadequate in any circumstances.

As has been indicated, the invention may be used for establishing a magnetization level for leakage field testing other than by the magnetic particle method. It may be used, for example, in a testing arrangement as diagrammatically illustrated in FIG. 6, using equipment generally designated by reference numeral 56 for testing of pipe 57 having a longitudinally extending welded portion 58. The pipe 57 is disposed between a pair of pole portions 59 and 60 of a yoke structure 62, magnetizing coils 63 and 64 being wound on the pole portions 59 and 60 and being connected through a reversing switch 65 to an adjustable current source 66 having an adjustment knob 67, the source being connected through lines 68 and a switch 69 to an AC supply. A leakage field probe 70 is connected to detector circuitry 71 to detect any leakage fields produced across the seam 58. To establish the proper level of magnetization, the instrument 18 may be used in the same way as described above. Thus the pipe 57 may be placed in a demagnetized condition and a surface portion over the welded portion 58 may be prepared, as by removing scale, after which the probe 19 may be placed thereon with the current source 67 being then energized and adjusted until the target indication is produced. For detection of flaws deep within the wall of the pipe, for example, flaws extending to the inside surface of the pipe, it may be desirable to increase the magnetization level above the target level determined as set forth above. By way of example, the level of magnetization may be increased to produce an eddy current response of from 2 to 3 times the eddy current response in the manner as set forth above.

It will be understood that modification and variations may be effected without departing from the spirit and scope of the novel concepts of this invention.

I claim as my invention:

1. In a method of testing parts of various types of ferromagnetic material through detection of leakage fields at the surfaces of the parts for indication of defects therein, the steps of providing an eddy current testing instrument including probe means and including indicating means so calibrated as to produce a certain target indication under a reproducible standard condition, preparing at least a representative part of each type tested by establishing a demagnetized condition thereof and by establishing base metal characteristics at at least one surface portion thereof, placing said probe means against the said surface portion of each prepared part, adjustably applying a uni-directional magnetic field to each prepared part to establish a certain field level at which said target indication is produced, and testing all parts of the same type by applying a magnetic field at said certain field level while detecting leakage fields at surface portions thereof, said target indication and said reproducible standard indication being such that a magnetic field at said certain field level produces uniformly detectable leakage fields from shallow seams in any part of ferromagnetic material tested regardless of the type of ferromagnetic material of the part.

2. In a method as defined in claim 1, wherein said indicating means is arranged to produce a certain calibration indication having a predetermined relation to said certain target indication, the step of providing a standard test block of ferromagnetic material having a slot therein of a certain size, and checking the calibration of said indicating means by placing said probe means on said test block over said slot while adjusting the sensitivity of said eddy current instrument to produce said certain calibration indication.

3. In a method as defined in claim 1, wherein said indicating means is arranged to produce a certain balance indication, the step of adjusting said instrument to produce said balance indication while placing said probe means against said surface portion of a prepared part prior to applying said magnetic field thereto.

4. In a method as defined in claim 1, said detecting of leakage fields being performed by dispersing magnetic particles over the surface thereof during the application of a unidirectional magnetic field at said certain field level.

5. In a method as defined in claim 1, said detecting of leakage fields being performed by providing a leakage field detector including a sensing probe, and engaging said probe with the part while applying a uni-directional magnetic field at said certain field level.

* * * * *